United States Patent [19]

Bollinger et al.

[11] 4,179,466
[45] Dec. 18, 1979

[54] PHTHALIC DIANILIDES

[75] Inventors: Frederic G. Bollinger; John J. D'Amico, both of St. Louis, Mo.

[73] Assignee: Monsanto Company, St. Louis, Mo.

[21] Appl. No.: 959,286

[22] Filed: Nov. 9, 1978

Related U.S. Application Data

[62] Division of Ser. No. 546,236, Feb. 3, 1975, abandoned.

[51] Int. Cl.$^2$ .................. A01N 5/00; A01N 9/20; C07C 103/78; C07C 103/76
[52] U.S. Cl. .................. 260/558 A; 71/76; 71/111; 71/118; 260/558 P; 560/48
[58] Field of Search .............. 260/558 A, 558 P; 71/118; 560/48

[56] References Cited

U.S. PATENT DOCUMENTS

| | | | |
|---|---|---|---|
| 2,057,145 | 10/1936 | Haffner et al. | 260/558 A X |
| 3,049,518 | 8/1962 | Stephens | 260/558 A X |
| 3,296,303 | 1/1967 | Nemec et al. | 260/558 A |
| 3,389,166 | 6/1968 | Loev | 260/558 A X |
| 3,502,685 | 3/1970 | Geirrtz et al. | 71/118 X |
| 3,549,348 | 12/1970 | Geirrtz et al. | 71/118 X |
| 3,658,892 | 4/1972 | Martin et al. | 71/115 X |
| 3,720,712 | 3/1973 | Largman | 260/558 A |
| 3,853,530 | 12/1974 | Franz | 71/76 |
| 3,947,263 | 3/1976 | Brouwer et al. | 71/76 |

OTHER PUBLICATIONS

Isogai et al., CA 79:112288n (1973).
Shindy et al., CA 79:155368k.

*Primary Examiner*—Thomas A. Waltz
*Attorney, Agent, or Firm*—Richard H. Shear; Donald W. Peterson

[57] ABSTRACT

Compounds having the formula

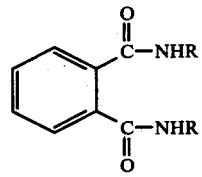

are found to be effective in regulating the growth of leguminous plants.

4 Claims, No Drawings

PHTHALIC DIANILIDES

This is a division of application Ser. No. 546,236 filed Feb. 3, 1975, now U.S. Pat. No. 4,146,386.

The invention relates to a new class of chemical compounds and their use as plant growth regulants. More specifically, the invention relates to novel phthalic dianilides useful in regulating the growth of leguminous plants.

Phthalic dianilides useful in accordance with this invention are represented by the formula

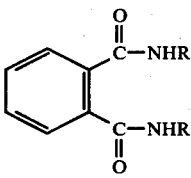

wherein R is trifluoromethylphenyl, chlorotrifluoromethylphenyl, 3',5'-dimethoxyphenyl, dichlorophenyl or methylbenzoate. A preferred embodiment of the invention are the phthalic dianilides of the above formula in which R is 3'-trifluoromethylphenyl, 2'-chloro-5'-trifluoromethylphenyl or 3',5'-dimethoxyphenyl.

The term "plant regulant", as employed in this application, connotes a material which serves to modify the normal sequential development of a desirable crop plant to agricultural maturity. Such modification may result from the effect of the material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alteration, increased branching, tillering, terminal inhibition, increased flowering or fruit set, increased root growth, stool or sprout inhibition, delayed budding, defoliation, desiccation, delayed senescence, prolongated dormancy, increased cold hardiness, delayed or accelerated ripening, thinning of fruit, prevention of pre-harvest fruit drop, loosening of fruit and the like.

Modification in the normal sequential development of a treated plant to agricultural maturity may also be manifested by reduced transpiration or increased carbohydrate deposition or protein content.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Further, a reduction in the maturation rate on portions of a crop permits an extended harvest period at peak yield and more efficient use of subsequent crop processing equipment.

It is to be understood that the regulation of desirable crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of plants is achieved by applying the above-described plant regulants to seeds, emerging seedlings, roots, stems, leaves, flowers, fruits or other plant parts. Such application may be made directly to the plant part, or indirectly by application to the plant growing medium.

The term "active ingredient" will be used hereinafter in this specification to describe the active phthalic dianilides of the foregoing formula. In practicing the plant growth regulating methods of this invention, the active ingredients can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

Illustrative finely divided solid carriers and extenders which are useful in the plant growth regulating compositions of this invention, include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents include, for example, Stoddard solvent, acetone, alcohols, glycols, ethyl acetate, benzene and the like. The plant growth regulating compositions of this invention, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonate, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total compositions. If desired, from about 0.1 to 2.0 parts by weight of the solid inert extender can be replaced by a corrosion inhibitor or anti-foaming agent.

Aqueous suspensions can be prepared by mixing together and grinding an aqueous slurry of water-insoluble active ingredient in the presence of dispersing agents to obtain a concentrated slurry of finely-divided particles. The resulting concentrated aqueous suspension is characterized by its extremely small particle size, so that when diluted and sprayed uniform coverage is obtained.

Emulsifiable oils are usually solutions of active ingredient in water-immiscible or partially water-immiscible solvents together with surface-active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface-active agent and about 4 to 94 parts solvent, all parts being by weight based on the total weight of emulsifiable oil.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. The application of the plant growth regulating compositions to the plant growth medium is generally carried out by incorporating the compositions in the soil or other media in the area where modification of the plants is desired.

In selecting the appropriate non-toxic rate of application of the active ingredient it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts from about 0.05 to about 10 or more pounds per acre. Foliar applications of from 0.1 to 5 pounds of the active ingredient per acre are preferred. In applications to the soil habitat of germinant seeds, emerging seedlings, and established vegetation for the regulation of plant growth, the active ingredients are applied in amounts of from about 0.01 to about 20 pounds per acre or more. Preferably, the active ingredients are applied to the soil at a rate of from 0.1 to 10 pounds per acre. Foliar application to plants beginning to blossom is particularly advantageous and is preferred.

In accordance with the present invention, the novel phthalic dianilides are found to be effective growth regulators for leguminous plants, as represented by soybean (Glycine max). Plants treated with the novel phthalic dianilides exhibit a reduction in stature as well as axillary bud development. Other differences are noted as well. By reducing the stature of the plant, the growing energy utilized by the plant is directed more toward fruiting and less toward vegetative growth. This causes an increase in the plant's efficiency of production as well as an increase in the number of plants per unit area providing for an optimization of crop output. Further, shorter plants undergo less lodging. Thus, when harvested, less plants are lost and the yield is increased.

In accordance with the practice of the invention, several plant growth regulating compositions were formulated utilizing several of the novel phthalic dianilides as the active ingredient. The compositions were formulated so that they could be applied at a rate the equivalent of 200 gallons per acre (306 liters per hectare). Table I illustrates the formulation of the composition for several application rates of active ingredient. The formulation of the composition for other rates of application is well within the skill of the art. In each formulation, the stock solution utilized is 1% of the active ingredient dissolved in acetone.

TABLE I

| RATE Lbs/Acre | (kilos/ hectare) | ml of 1% Stock Solution | ml Acetone | ml of 0.39% TWEEN 20 In Water As Surfactant |
|---|---|---|---|---|
| 6.0 | (6.72) | 2.0 | — | 3.6 |
| 5.0 | (5.60) | 2.0 | 1.0 | 3.7 |
| 3.0 | (3.36) | 1.0 | 1.0 | 3.6 |
| 2.5 | (2.80) | 1.0 | 2.0 | 3.7 |
| 1.2 | (1.34) | 0.4 | 1.6 | 3.6 |
| 1.0 | (1.12) | 0.4 | 2.6 | 3.7 |
| 0.6 | (0.672) | 0.2 | 1.8 | 3.6 |
| 0.5 | (0.560) | 0.2 | 2.8 | 3.7 |
| 0.3 | (0.336) | 0.1 | 1.9 | 3.6 |

Utilizing compositions formulated in accordance with TABLE I, several phthalic dianilides exhibited unexpected plant growth regulating properties as illustrated by the test set forth in Example 1.

EXAMPLE 1

A number of soybean plants, variety Corsoy, are grown from seeds in aluminum pans in a greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. An aqueous composition of the active ingredient is then applied to the pan of growing plants by overhead spray at a rate equivalent to 6 pounds of chemical per acre. The treated pans, along with the control pans, are maintained in a greenhouse and watered from below on a sand bench and fertilized with a uniform portion of a water-soluble balanced fertilizer.

Two weeks after application of the chemical the average height of the soybean plants in the treated pan is again measured as above and the difference in the average height before and two weeks after application represent the increase in the development of the treated plants. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction or an increase in growth in excess of 25% of that of the control plants, i.e., growth stimulation.

Table II summarizes the results and observations made in accordance with Example 1 when the phthalic dianilides of the formula

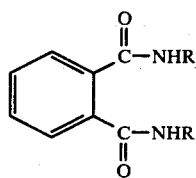

are utilized as the active ingredient at several application rates.

soil. Two pots of 6-week old plants (5-6 trifoliate stage) are used for each application of the chemical. An overhead spray of an aqueous composition in which the active ingredient is a phthalic dianilide of the foregoing formula in which R is either 3'-trifluoromethylphenyl or 3',5'-dimethoxyphenyl is applied to the pots at an equivalent rate as indicated below. Two to four sets of plants which received no chemical application are included and serve as controls. All of the pots are maintained under good growing conditions and are watered and are uniformly fertilized with a uniform amount of a water-soluble balanced fertilizer. Two weeks after the application of the chemical the growth response of the treated plants is compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations on other plant modifications, e.g., canopy shape, axillary bud development and the

TABLE II

| Active Ingredient (R) | RATE Lbs/Acre | (Kilos/Hectare) | Result |
|---|---|---|---|
| 3'-trifluoromethylphenyl | 6.0 | (6.72) | Stature Reduction, Axillary Bud Development, Rosette Growth |
| 3'-trifluoromethylphenyl | 3.0 | (3.36) | Stature Reduction, Axillary Bud Development, Rosette Growth, Leaf Inhibition |
| 3'-trifluoromethylphenyl | 1.2 | (1.34) | Stature Reduction, Axillary Bud Development, Rosette Growth |
| 3'-trifluoromethylphenyl | 0.6 | (0.672) | Stature Reduction, Axillary Bud Development, Altered Canopy |
| 2'-chloro-5'-trifluoromethylphenyl | 6.0 | (6.72) | Stature Reduction, Axillary Bud Development, Altered Canopy |
| 2'-chloro-5'-trifluoromethylphenyl | 3.0 | (3.36) | Axillary Bud Development |
| 2'-chloro-5'-trifluoromethylphenyl | 1.2 | (1.34) | None |
| 3',5'-dimethoxyphenyl | 6.0 | (6.72) | Stature Reduction, Axillary Bud Development, Rosette Growth, Slight Leaf Burn |
| 3',5'-dimethoxyphenyl | 3.0 | (3.36) | Stature Reduction, Axillary Bud Development, Rosette Growth, Slight Leaf Burn |
| 3',5'-dimethoxyphenyl | 1.2 | (1.34) | Stature Reduction, Axillary Bud Development, Rosette Growth, Slight Leaf Burn |
| 3',5'-dimethoxyphenyl | 0.6 | (0.672) | Stature Reduction, Axillary Bud Development, Rosette Growth, Slight Leaf Burn |
| 3',5'-dimethoxyphenyl | 0.3 | (0.336) | Stature Reduction, Axillary Bud Development, Rosette Growth |

Further advantages of this invention are shown in Example 2.

EXAMPLE 2

Individual soybean plants, variety Wayne, are grown from seed in 6 inch pots containing a good grade of top like are noted.

The treated plants exhibited a reduction in stature. Further results noted are summarized in Table III.

TABLE III

| Active Ingredient (R) | RATE Lbs/Acre | (Kilos/Hectare) | Result |
|---|---|---|---|
| 3'-trifluoromethylphenyl | 1.0 | (1.12) | Chlorosis, Inhibited Pod Set, Leaf Inhibition, Axillary Bud Development, Altered Canopy |
| 3'-trifluoromethylphenyl | 0.5 | (.560) | Chlorosis, Dark Foliar Color, Axillary Bud Development, Altered Canopy |
| 3'-trifluoromethylphenyl | 0.25 | (.280) | Dark Foliar Color, Axillary Bud Development, Altered Canopy |
| 3',5'-dimethoxyphenyl | 0.5 | (.560) | Epinasty, Leaf Distortion, Rosette Growth |
| 3',5'-dimethoxyphenyl | 0.25 | (.280) | Epinasty, Leaf Distortion |
| 3',5'-dimethoxyphenyl | 0.1 | (.112) | Leaf Distortion |

A preferred embodiment of the invention is the phthalic dianilide in which R is 3'-trifluoromethylphenyl having the following formula

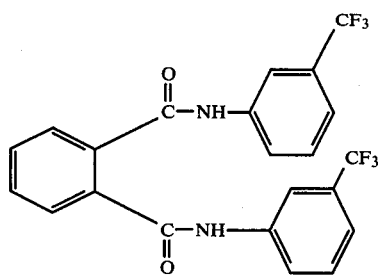

This compound was tested in the manner described by Example 3.

EXAMPLE 3

Individual soybean plants, variety Wayne, are grown from seed in 6 inch pots containing a good grade of top soil. Three soybean plants, one per pot, which have reached the 4th trifoliate stage (4–5 weeks after planting) are used for each application of the chemical. An overhead spray of a composition containing the active ingredient is applied to the pots at the rates indicated below. Two to four sets of plants which received no chemical application are included to serve as controls. All of the pots are maintained under good growing conditions, are watered and are uniformly fertilized with a uniform amount of a water-soluble balanced fertilizer. Four to seven days after application of the active ingredient the photosynthetic response of the treated plants is compared with that of the control plants by placing the second trifoliate leaf of the soybean plant in a chamber, which is uniformly illuminated from above, introducing into the chamber air in which the $CO_2$ concentration, temperature and relative humidity have been carefully controlled and measuring the difference between the $CO_2$ concentration of the air entering the chamber and that leaving the chamber. Three plants are used to determine an average response which is compared to the average response of the control plants. When the active ingredient utilized was a compound of the formula

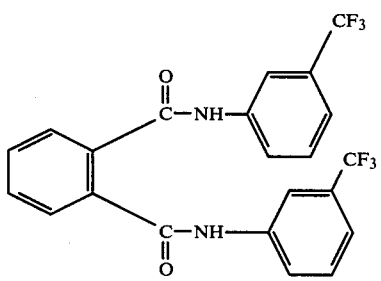

the following responses were obtained.

At an application rate of 2.5 pounds per acre, the photosynthetic response was inhibition of $CO_2$ uptake by the plant of from 15 to 29.99 percent of the control. Chlorosis, rosette growth and axillary bud development was found as well.

At an application rate of 0.5 pounds per acre, the photosynthetic response was stimulation of $CO_2$ uptake by the plant ranging from 15 to 29.99 percent of the control along with chlorosis, rosette growth, axillary bud development and canopy shape alteration.

At an application rate of 1.65 pounds per acre, inhibition of $CO_2$ uptake of the plant ranging from 15 to 29.99 percent of the control along with rosette growth, inhibition of apical development and stature reduction was exhibited.

Generally, the novel phthalic dianilides are prepared by the following reaction:

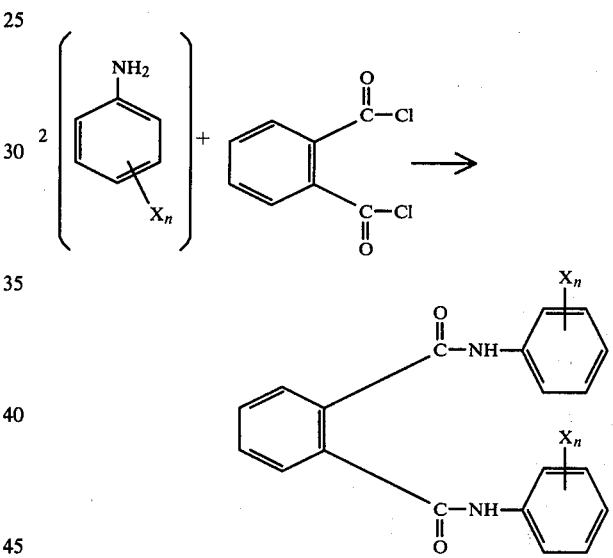

The preparation of the novel phthalic dianilides may be more fully illustrated by the following example.

EXAMPLE 4

To a stirred solution containing 0.5 mole of the appropriate substituted aniline in 300 ml. of benzene, 20.3 g. (0.1 mole) of phthaloyl chloride is added in one portion. The exothermic reaction causes a temperature rise of about 20° to 25° C. The reaction mixture is then stirred at 25°–30° C. for a time period ranging from 1 to 24 hours. The time period required for each aniline is set out in TABLE IV, below. The precipitate is collected by filtration, washed successively with 200 ml. of benzene, 200 ml. of ethylether and finally with one liter of water and air-dried at 25°–30° C.

TABLE IV lists the data obtained when the phthalic dianilides of the invention were prepared in accordance with Example 4.

TABLE IV

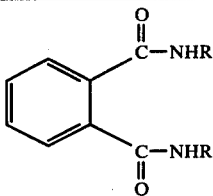

| R | Time Of Reaction (hrs) | % Yield Crude | mp °C. | Empirical Formula | % C Calcd./Found | | % H Calcd./Found | | % N Calcd./Found | | % F Calcd./Found | |
|---|---|---|---|---|---|---|---|---|---|---|---|---|
| 3-CF$_3$-phenyl | 1 | 47 | 252 (a) | C$_{22}$H$_{14}$F$_6$N$_2$O$_2$ | — | — | — | — | 6.19 | 6.30 | 25.20 | 25.42 |
| 3-Cl,4-CF$_3$-phenyl (2'-Cl, 5'-CF$_3$) | 5 | 31 | 211-2 (b) | C$_{22}$H$_{12}$Cl$_2$F$_6$N$_2$O$_2$ | 50.69 | 50.74 | 2.32 | 2.26 | 5.37 | 5.30 | — | — |
| 3,5-(OCH$_3$)$_2$-phenyl | 24 | 100 | 196-7 (c) | C$_{24}$H$_{24}$N$_2$O$_6$ | 66.04 | 65.82 | 5.54 | 5.49 | 6.42 | 6.35 | — | — |
| 3,4-Cl$_2$-phenyl | 24 | 99 | 268-70 | C$_{20}$H$_{12}$Cl$_4$N$_2$O$_2$ | 52.90 | 52.52 | 2.66 | 2.67 | 6.17 | 6.24 | — | — |
| 3-COOCH$_3$-phenyl | 24 | 93 | 219-20 (b) | C$_{24}$H$_{20}$N$_2$O$_6$ | 66.66 | 66.77 | 4.66 | 4.67 | 6.48 | 6.39 | — | — |

NOTE:
(a) Recrystallization from isopropyl alcohol
(b) Recrystallization from toluene
(c) Recrystallization from methyl alcohol The phthalic dianilides described herein exhibit unexpected properties when used to regulate the growth of desirable crop plants, especially leguminous plants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows.

What is claimed is:

1. A compound having the formula

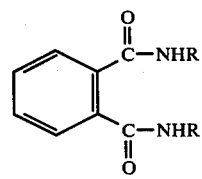

wherein R is selected from the group consisting of 3'-trifluoromethylphenyl, 2'-chloro-5'-trifluoromethylphenyl and 3',5'-dimethoxyphenyl.

2. A compound in accordance with claim 1 wherein R is 3'-trifluoromethylphenyl.

3. A compound in accordance with claim 1 wherein R is 2'-chloro-5'-trifluoromethylphenyl.

4. A compound in accordance with claim 1 wherein R is 3',5'-dimethoxyphenyl.

* * * * *